(12) United States Patent
Yoshiki et al.

(10) Patent No.: US 8,222,393 B2
(45) Date of Patent: Jul. 17, 2012

(54) POLYPEPTIDE USEFUL FOR CANCER DIAGNOSIS AND TREATMENT

(75) Inventors: Tatsuhiro Yoshiki, Otsu (JP); Susumu Kageyama, Kyoto (JP); Masamichi Ueda, Osaka (JP)

(73) Assignee: TSS Biotech Inc., Tokyo (JP)

( * ) Notice: Subject to any disclaimer, the term of this patent is extended or adjusted under 35 U.S.C. 154(b) by 704 days.

(21) Appl. No.: 11/628,056

(22) PCT Filed: Feb. 1, 2005

(86) PCT No.: PCT/JP2005/001736
§ 371 (c)(1),
(2), (4) Date: Nov. 30, 2006

(87) PCT Pub. No.: WO2005/118811
PCT Pub. Date: Dec. 15, 2005

(65) Prior Publication Data
US 2008/0089882 A1    Apr. 17, 2008

(30) Foreign Application Priority Data
Jun. 2, 2004 (JP) .................. 2004-164844

(51) Int. Cl.
C07H 21/02 (2006.01)
C07H 21/04 (2006.01)
C07H 21/00 (2006.01)
A01N 63/00 (2006.01)

(52) U.S. Cl. ................ 536/24.5; 536/23.1; 536/24.3

(58) Field of Classification Search .............. None
See application file for complete search history.

(56) References Cited

U.S. PATENT DOCUMENTS

| | | | |
|---|---|---|---|
| 6,132,973 A | 10/2000 | Lal et al. | |
| 6,504,010 B1 * | 1/2003 | Wang et al. | 530/350 |
| 2003/0008284 A1 | 1/2003 | Kennedy et al. | |
| 2003/0108963 A1 | 6/2003 | Schlegel et al. | |
| 2003/0124128 A1 | 7/2003 | Lillie et al. | |

FOREIGN PATENT DOCUMENTS

| | | |
|---|---|---|
| JP | 7-51065 A | 6/1995 |
| JP | 2000-511536 A | 9/2000 |
| WO | WO-97/45445 A1 | 12/1997 |
| WO | WO-00/55174 | 9/2000 |
| WO | WO-00/60073 A1 | 10/2000 |
| WO | WO 01/96523 * | 12/2001 |
| WO | WO-01/96523 A2 | 12/2001 |
| WO | WO 02/31111 * | 1/2002 |
| WO | WO-02/059271 A2 | 8/2002 |
| WO | WO-02/059271 A3 | 8/2002 |
| WO | WO-03/004989 A2 | 1/2003 |
| WO | WO-03/009814 A2 | 2/2003 |

OTHER PUBLICATIONS

Ezzell (J. NIH Res, 1995, 7:46-49).*
Spitler (Cancer Biotherapy, 1995, 10:1-3).*
Boon (Adv Can Res, 1992, 58:177-210).*
DeGruijl et al (Nature Medicine, 5410): 1124-1125, Oct. 1999).*
Bodey et al (Anticancer Research. 20:2665-2676; 2000).*
Gaiger et aL (Blood, vol. 96, No. 4, Aug. 2000, pp. 1480-1489).*
Orkin and Motulsky (NIH ad hoc committee Dec. 1995 http://www.nih.gov/news/pane/rep.html, p. 1).*
Theodore Friedmann (Scientific American Jun. 1997, p. 96-101).*
Inder Verma (Nature Sep. 1997;389:239-242).*
Rubanyi (Molecular Aspects of Medecine 2001 ;22:113-142).*
Tiemann, K., et al. (2009) RNAi-based terapeutics-current status, challenges and prospects. EMBO Molecular Medicine, v. 1:142-151.*
Yu, A. (2007) Small Interfering RNA in Drug Metabolism and Transport. Current Drug Metabolism, v.8:700-708.*
Azumi, et al. (2009) Localization and Characterization of Gamma-glutamyl Cycotransferase in Cancer Cells, Molecular Medicine Reports, V.2:385-91.*
Strausberg, R.L. et al., Database SwissProt Accession No. 075223, Sep. 15, 2003, Protein C7orf24.
Kageyama et al., The American Association for Clinical Chemistry, vol. 50, No. 5, Feb. 5, 2004, pp. 857-866.
Greenbaum, et al., Genome Research, (2001), vol. 11, No. 9, pp. 1463-1468.
Xu X-R et al., "Insight into hepatocellular carcinogenesis at transcriptome level by comparing gene expression profiles of hepatocellular carcinoma with those of corresponding noncancerous liver," Proceedings of the National Academy of Sciences of USA, National Academy of Science, Washington, D.C., US, vol. 98, No. 26, pp. 15089-15094, XP002231180, Dec. 18, 2001 = pub. date.
Mowry, K.L. et al., "Identification of the Human U7 snRNP as One of Several Factors Involved in the 3' End Maturation of Histone Premessenger RNA's," Science, vol. 238, No. 4834, 1987, pp. 1682-1687, XP-002454373.

* cited by examiner

*Primary Examiner* — Jennifer Pitrak McDonald
(74) *Attorney, Agent, or Firm* — Birch, Stewart, Kolasch & Birch, LLP (57) ABSTRACT

The present invention provides a method capable of effectively detecting cancer by finding a novel cancer marker. The present invention also provides a pharmaceutical composition for preventing or treating cancer. The present invention relates to a method for detecting cancer by detecting the expression of a U7 polypeptide in a sample derived from a test subject.

7 Claims, 4 Drawing Sheets

The number of days after infection with retrovirus

Fig. 4

POLYPEPTIDE USEFUL FOR CANCER DIAGNOSIS AND TREATMENT

This application is a national stage entry of PCT application number PCT/JP2005/001736 filed on Feb. 1, 2005, which claims priority to Japanese patent application number 2004-164844, filed Jun. 2, 2004.

TECHNICAL FIELD

The present invention relates to a polypeptide useful for cancer diagnosis, a method for detecting cancer by detecting the expression of the polypeptide, a cell growth inhibitor comprising a reagent inhibiting the function or expression of the polypeptide, and a pharmaceutical composition for treating or preventing cancer comprising the cell growth inhibitor.

BACKGROUND ART

Cancers such as lung cancer, colon cancer, breast cancer, prostatic cancer, uterine cancer, choriocarcinoma, bladder cancer, kidney cancer, thyroid cancer, parotid gland cancer, head and neck cancer, brain tumor, bone and soft tissue sarcomas, ureteral cancer, liver cancer, ovarian cancer, fallopian tube cancer, esophagus cancer, and gastric cancer are all malignant tumors and are, particularly if progressive, difficult to treat and often fatal. Thus, the most important challenge as a measure against cancer is the early detection of carcinomas.

Tumor markers such as CEA and CA19-9 have previously been reported and used in the diagnosis of such cancers and the observation of the prognosis. However, each of them has a positive rate on the order of only 20 to 30%, and most markers exhibit negative particularly for early stage cancer. Moreover, outcomes from therapies for advanced cancer are poor as described above, and early detection brings about the greatest effect. Therefore, it has been expected to find a novel and useful tumor marker. For example, those described in JP Patent Publication (Kokai) No. 7-51065A (1995), WO00/060073, and JP Patent Publication (Kohyo) No. 2000-511536A (2000) have been known as molecular biological methods of diagnosis using antigenic protein markers.

The surgical excision of cancer tissues, the systemic administration of anticancer agents, and so on has been performed as cancer therapies. However, these therapies are less effective for cancer that has entered an advanced stage, as described above, and also present the problem of a significant physical burden on patients even if their cancers are found early.

DISCLOSURE OF THE INVENTION

An object of the present invention is to provide a method capable of effectively detecting cancer by finding a novel cancer marker and to provide a pharmaceutical composition for preventing or treating cancer.

The present inventors have conducted diligent studies for attaining the object and have consequently completed the present invention by finding out that one of hypothetical polypeptides is actually expressed in cells and that this polypeptide is overexpressed in a manner specific to cancer cells, and cancer cell growth can be suppressed by inhibiting the function or expression of the polypeptide.

Namely, the present invention encompasses the following inventions:

(1) A method for detecting cancer by detecting the expression of a U7 polypeptide in a sample derived from a test subject.

(2) The method according to (1), wherein the expression of the U7 polypeptide in the sample is immunologically measured with an antibody specifically reacting with the U7 polypeptide or a fragment thereof.

(3) A diagnostic drug for cancer comprising a reagent for detecting the expression of a U7 polypeptide.

(4) The diagnostic drug for cancer according to (3), wherein the reagent for detecting the expression of a U7 polypeptide is an antibody specifically reacting with the U7 polypeptide or a fragment thereof.

(5) The diagnostic drug for cancer according to (3) or (4), wherein the cancer is selected from the group consisting of lung cancer, colon cancer, gastric cancer, prostatic cancer, uterine cancer, choriocarcinoma, and urothelial cancer.

(6) A kit for cancer diagnosis comprising the diagnostic drug for cancer according to any one of (3) to (5).

(7) A cell growth inhibitor comprising a reagent inhibiting the function or expression of a U7 polypeptide as an active ingredient.

(8) The cell growth inhibitor according to (7), wherein the reagent inhibiting the function or expression of a U7 polypeptide is an antibody against the U7 polypeptide.

(9) The cell growth inhibitor according to (7), wherein the reagent inhibiting the function or expression of a U7 polypeptide is double-stranded RNA decreasing a U7 polypeptide-encoding mRNA level through RNA interference.

(10) The cell growth inhibitor according to (7), wherein the reagent inhibiting the function or expression of a U7 polypeptide is DNA encoding double-stranded RNA decreasing a U7 polypeptide-encoding mRNA level through RNA interference.

(11) The cell growth inhibitor according to (9) or (10), wherein the double-stranded RNA decreasing a U7 polypeptide-encoding mRNA level through RNA interference is double-stranded RNA consisting of RNA comprising a nucleotide sequence having at least 80% homology to the nucleotide sequence represented by SEQ ID NO: 1 and RNA comprising a nucleotide sequence having at least 80% homology to the nucleotide sequence represented by SEQ ID NO: 2.

(12) A pharmaceutical composition for treating or preventing cancer comprising a cell growth inhibitor according to any one of (7) to (11).

(13) The pharmaceutical composition according to (12), wherein the cancer is selected from the group consisting of lung cancer, colon cancer, gastric cancer, prostatic cancer, uterine cancer, choriocarcinoma, and urothelial cancer.

(14) Double-stranded RNA consisting of RNA comprising a nucleotide sequence having at least 80% homology to the nucleotide sequence represented by SEQ ID NO: 1 and RNA comprising a nucleotide sequence having at least 80% homology to the nucleotide sequence represented by SEQ ID NO: 2.

(15) DNA encoding double-stranded RNA according to (14).

(16) A vector comprising DNA according to (15).

(17) A protein of the following (a) or (b):
(a) a protein comprising the amino acid sequence represented by SEQ ID NO: 13; and
(b) a protein comprising an amino acid sequence derived from the amino acid sequence represented by SEQ ID NO: 13 with the deletion, substitution, or addition of one or several amino acids, wherein an antibody obtained by immunizing an animal with the protein as an antigen specifically reacts with the protein (a).

(18) A gene encoding a protein of the following (a) or (b):
(a) a protein comprising the amino acid sequence represented by SEQ ID NO: 13; and
(b) a protein comprising an amino acid sequence derived from the amino acid sequence represented by SEQ ID NO: 13 with the deletion, substitution, or addition of one or several amino acids, wherein an antibody obtained by immunizing an animal with the protein as an antigen specifically reacts with the protein (a).

(19) A gene comprising DNA of the following (a) or (b):
(a) DNA consisting of the nucleotide sequence represented by SEQ ID NO: 14; and
(b) DNA hybridizing under stringent conditions to DNA consisting of a nucleotide sequence complementary to DNA consisting of the whole or a portion of the nucleotide sequence represented by SEQ ID NO: 14, wherein an antibody obtained by immunizing an animal with a protein encoded by the DNA as an antigen specifically reacts with a protein encoded by the DNA (a).

Hereinafter, the present invention will be described in detail.

1. U7 Polypeptide

The present inventors have compared normal cells and a variety of cancer cells and have consequently found a novel polypeptide that is remarkably overexpressed in cancer cells as compared with normal cells. The present inventors have found that the polypeptide is a hypothetical polypeptide C7orf24 on the polypeptide database, and have identified this polypeptide as a U7 polypeptide. Although the U7 polypeptide (C7orf24) has been known so far only as a hypothetical polypeptide, the present inventors have found for the first time that the polypeptide is actually expressed in cells and is overexpressed in cancer cells as compared with normal cells. The amino acid sequence (SEQ ID NO: 13) of the U7 polypeptide and the DNA sequence (SEQ ID NO: 14) encoding the polypeptide have been recorded as Swiss-Prot primary accession number: 075223 and GenBank accession number: NM_024051 (Protein name: Protein C7orf24, Gene name: C7ORF24).

The U7 polypeptide encompasses a protein comprising an amino acid sequence derived from the amino acid sequence represented by SEQ ID NO: 13 with the deletion, substitution, or addition of one or several amino acids, wherein an antibody obtained by immunizing an animal with the protein as an antigen specifically reacts with the protein comprising the amino acid sequence represented by SEQ ID NO: 13. In this context, "several" amino acids mean usually two to five, preferably two to three amino acids. The animal to be immunized is not particularly limited and is preferably a mammal.

A gene encoding the U7 polypeptide encompasses DNA hybridizing under stringent conditions to DNA consisting of a nucleotide sequence complementary to DNA consisting of the whole or a portion of the nucleotide sequence represented by SEQ ID NO: 14, wherein an antibody obtained by immunizing an animal with a protein encoded by the DNA as an antigen specifically reacts with a protein encoded by the DNA consisting of the nucleotide sequence represented by SEQ ID NO: 14.

The stringent conditions refer to conditions in which specific hybrids are formed but no nonspecific hybrids are formed. Namely, the stringent conditions refer to conditions under which DNA having high homology (90% or more, preferably 95% or more homology) to the gene of the present invention can hybridize. To be more specific, such conditions can be achieved by performing hybridization at 42 to 68° C. in the presence of 0.5 to 1 M NaCl or at 42° C. in the presence of 50% formamide or at 65 to 68° C. in an aqueous solution and then washing a filter at room temperature to 68° C. with 0.1 to 2-fold concentration of SSC (saline sodium citrate) solution.

In this context, the "sequence of a portion" refers to the nucleotide sequence of DNA comprising a portion of the nucleotide sequence of the gene, wherein the DNA encodes a protein that produces, when used as an antigen to immunize an animal, an antibody specifically reacting with the U7 polypeptide. Moreover, the "sequence of a portion" is a nucleotide sequence with a length sufficient to hybridize under stringent conditions and is, for example, an at least 10-base, preferably at least 50-base, more preferably at least 200-base sequence.

In the present invention, the "polypeptide" means a molecule composed of several amino acid residues bound together through amide bond (peptide bond) and encompasses proteins and oligopeptides. Moreover, the "antibody" means a polyclonal or monoclonal antibody produced with the U7 polypeptide or a fragment thereof as an immunogen.

Various techniques used for carrying out the present invention, except when the source of a technique is named otherwise, are practicable with ease and reliability by those skilled in the art on the basis of documents and so on known in the art. For example, the preparation of agents for preparing pharmaceutical drugs according to the present invention is described in Remington's Pharmaceutical Sciences, 18th Edition, ed. A. Gennaro, Mack Publishing Co., Easton, Pa., 1990, and genetic engineering and molecular biological techniques are described in Sambrook and Maniatis, Molecular Cloning—A Laboratory Manual, Cold Spring Harbor Laboratory Press, New York, 1989; and Ausubel, F. M. et al., Current Protocols in Molecular Biology, John Wiley & Sons, New York, N.Y., 1995.

2. Cancer Detection

The present invention relates to a method for detecting cancer by detecting the expression of a U7 polypeptide in a sample derived from a test subject. The U7 polypeptide is expressed in a manner specific to cancer cells, as described above. Thus, cancer can be detected by detecting the expression of this U7 polypeptide in the sample derived from the test subject.

The method of the present invention is capable of detecting, preferably solid cancer including, but not limited to, lung cancer, colon cancer, breast cancer, prostatic cancer, uterine cancer, choriocarcinoma, kidney cancer, thyroid cancer, parotid gland cancer, head and neck cancer, brain tumor, bone and soft tissue sarcomas, liver cancer, ovarian cancer, fallopian tube cancer, esophagus cancer, gastric cancer, and urothelial cancer (renal pelvic cancer, ureteral cancer, bladder cancer, and urethral cancer). The method of the present invention can suitably be used for detecting, preferably lung cancer, colon cancer, gastric cancer, breast cancer, prostatic cancer, uterine cancer, choriocarcinoma, and urothelial cancer, more preferably urothelial cancer, even more preferably bladder cancer.

In this context, examples of a method for detecting the expression of a U7 polypeptide in a sample derived from a test subject include a method using (1) an antibody specifically reacting with the U7 polypeptide or a fragment thereof, (2) the U7 polypeptide, or (3) a probe or primer designed on the basis of a polynucleotide encoding the U7 polypeptide. Hereinafter, these means will be described in detail.

(1) Detection with Antibody Specifically Reacting with U7 Polypeptide or Fragment Thereof The antibody specifically reacting with the U7 polypeptide or a fragment thereof can bind to the U7 polypeptide expressed in cancer and can therefore be used to diagnose a sample as being derived or not derived from a patient with cancer or an individual at high risk for cancer by detecting its reaction with the U7 polypeptide in the sample.

The antibody specifically reacting with the U7 polypeptide or a fragment thereof is a polyclonal or monoclonal antibody, which can bind to the epitope of the U7 polypeptide. The globulin type of the antibody of the present invention is not particularly limited as long as it has the characteristics described above. It may be any of IgG, IgM, IgA, IgE, and IgD and is preferably IgG and IgM. The monoclonal antibody of the present invention particularly encompasses a "chimeric" antibody (immunoglobulin) where a portion of heavy chains and/or light chains is derived from a particular species or from a particular antibody class or subclass, and the remaining portion of the chains is derived from another species or from another antibody class or subclass, and also encompasses antibody fragments such as Fab, F(ab')$_2$, and Fv fragments as long as they have desired biological activity (U.S. Pat. No. 4,816,567; and Morrison et al, Proc. Natl. Acad. Sci. USA 81: 6851-6855 (1984)).

To produce the antibody of the present invention, a polypeptide serving as an immunogen (antigen) is prepared. The U7 polypeptide or a fragment thereof is used as the immunogenic polypeptide. In the present invention, the amino acid sequence of the U7 polypeptide available as an immunogen and the cDNA sequence encoding the polypeptide have been disclosed as Swiss-Prot primary accession number: 075223 and GenBank accession number: NM_024051 (Protein name: Protein C7orf24, Gene name: C7ORF24). Thus, the disclosed amino acid sequence information can be utilized to synthesize the U7 polypeptide or the fragment thereof for use as an immunogen by an approach known in the art, for example, a solid-phase peptide synthesis method. Examples of the fragment include a partial peptide consisting of at least 6 or more amino acids, preferably 6 to 500, more preferably 8 to 50 amino acids, in the U7 polypeptide. When the U7 polypeptide fragment is used as an immunogen, it is preferred that the fragment should be linked to a carrier protein such as KLH and BSA for use.

Moreover, a gene recombination approach known in the art may be utilized to produce the U7 polypeptide by using information on the cDNA encoding the U7 polypeptide. Hereinafter, the U7 polypeptide production using the recombination approach will be described.

A recombinant vector for U7 production can be obtained by ligating the disclosed cDNA sequence to an appropriate vector. A transformant can be obtained by introducing the recombinant vector for U7 production into a host so that the U7 polypeptide can be expressed.

A phage or plasmid capable of autonomously proliferating in a host microorganism is used as the vector. Examples of the plasmid DNA include Escherichia coli-derived plasmids (e.g., pET21a, pGEX4T, pUC118, pUC119, pUC18, and pUC19), Bacillus subtilis-derived plasmids (e.g., pUB110 and pTP5), and yeast-derived plasmids (e.g., YEp13, YEp24, and YCp50). Examples of the phage DNA include λ phages (e.g., λgt11 and λZAP). Furthermore, animal viruses such as vaccinia virus and insect viruses such as baculovirus can also be used.

To insert the U7 cDNA into the vector, for example, a method is adopted, wherein the purified DNA is initially cleaved with an appropriate restriction enzyme and inserted and ligated to the restriction site or multicloning site of an appropriate vector DNA.

In addition, the recombinant vector for U7 production used in a mammal cell may be ligated, if desired, with a cis-element (such as an enhancer), splicing signal, polyA-addition signal, selective marker, ribosome-binding sequence (SD sequence), and so on, in addition to a promoter and the U7 cDNA.

To ligate the DNA fragment to the vector fragment, DNA ligase known in the art is used. The DNA fragment and the vector fragment are ligated after annealing to produce the recombinant vector for U7 production.

The host used in transformation is not particularly limited as long as it can express the U7 polypeptide. Examples thereof include bacteria (e.g., Escherichia coli and Bacillus subtilis), yeast, animal cells (e.g., COS cells and CHO cells), and insect cells.

As an example, when the bacterium is used as a host, it is preferred that the recombinant vector for U7 production should be capable of autonomously replicating in the bacterium while composed of a promoter, a ribosome-binding sequence, the U7 DNA, and a transcription termination sequence. It may also contain a gene that controls the promoter. Examples of the Escherichia coli include Escherichia coli BRL. Examples of the Bacillus subtilis include Bacillus subtilis. Any promoter that can achieve expression in a host such as Escherichia coli may be used. A method for introducing the recombinant vector to the bacterium is not particularly limited as long as it is a method used for introducing DNA to bacteria. Examples thereof include a method using calcium ions and electroporation.

When yeast, an animal cell, an insect cell, or the like is used as a host, the U7 polypeptide can be produced in the same way as above according to an approach known in the art.

In the present invention, the U7 polypeptide used as an immunogen can be obtained by culturing the transformant thus prepared, followed by collection from the resulting cultured product. The "cultured product" means any of culture supernatants, cultured cells, cultured bacteria, and homogenates of the cells or the bacteria. A method for culturing the transformant in a medium is performed according to a usual method used in the culture of the host.

Both natural and synthetic media may be used as a medium for culturing the transformant obtained with a microorganism such as Escherichia coli and yeast as a host as long as they contain carbon sources, nitrogen sources, inorganic salts, and so on, which are capable of being assimilated by the microorganism, and can achieve the efficient culture of the transformant.

The culture is usually performed at 37° C. for 6 to 24 hours under aerobic conditions such as shake culture or aeration/agitation culture. pH is maintained around neutral values throughout the culture period. pH adjustment is performed with inorganic or organic acids, alkaline solutions, and so on. During the culture, an antibiotic such as ampicillin and tetracycline may be added, if necessary, to the medium.

When the U7 polypeptide is produced within the bacterium or the cell after the culture, the protein is extracted by disrupting the bacterium or the cell. Alternatively, when the U7 polypeptide is produced outside the bacterium or the cell, the culture solution is directly used or subjected to centrifugation or the like to remove the bacterium or the cell. Then, the U7 polypeptide can be isolated and purified from the cultured product by using, alone or in an appropriate combination, general biochemical methods used in protein isolation and purification, for example, ammonium sulfate precipitation, gel chromatography, ion-exchange chromatography, and affinity chromatography.

Whether or not the U7 polypeptide is obtained can be confirmed by SDS-polyacrylamide gel electrophoresis or the like.

The recombinant U7 polypeptide obtained by these procedures encompasses a fusion protein with any of other proteins. It can be exemplified by a fusion protein with glutathione S-transferase (GST) or green fluorescent protein (GFP). Furthermore, peptides expressed in transformed cells sometimes undergo a variety of post-translational modifications in the cells. Thus, the modified peptide can also be used as the U7 polypeptide. Such a post-translational modification can be exemplified by the elimination of N-terminal methionine, N-terminal acetylation, glycosylation, limited proteolysis by intracellular protease, myristoylation, isoprenylation, and phosphorylation.

Next, the obtained protein is dissolved in a buffer solution to prepare an immunogen. To effectively perform immunization, an adjuvant may be added thereto, if necessary. Examples of the adjuvant include commercially available complete and incomplete Freund's adjuvants. Any of them may be mixed therewith.

The monoclonal antibody may be produced by, for example, a hybridoma method (Kohler and Milstein, Nature (1975) 256: 495) or a recombination method (U.S. Pat. No. 4,816,567). Alternatively, it may be isolated from a phage antibody library (Clackson et al., Nature (1991) 352: 624-628; and Marks et al., J. Mol. Biol. (1991) 222: 581-597). For example, the monoclonal antibody can be prepared as described below.

i) Immunization and Collection of Antibody-Producing Cells

The immunogen thus obtained was administered to mammals, for example, rats, mice, (e.g., inbred BALB/c mice), or rabbits. One dose of the immunogen is appropriately determined depending on the types of immunized animals, administration routes, and so on and is however, approximately 50 to 200 μg per animal. The immunization is mainly performed by injecting the immunogen intravenously, hypodermically, or intraperitoneally. The time interval between immunizations is not particularly limited. After primary immunization, two to six, preferably three to four boosters are performed at several-day to several-week intervals, preferably one-week to four-week intervals. An antibody titer in the serum of the immunized animal is repetitively measured after the primary immunization by ELISA (Enzyme-Linked Immuno Sorbent Assay) or the like. When the antibody titer reaches a plateau, the immunogen is injected intravenously or intraperitoneally as the final immunization. After 2 to 5 days, preferably 3 days, from the final immunization, antibody-producing cells are collected. Examples of the antibody-producing cells include spleen cells, lymph node cells, and peripheral blood cells. Spleen cells or local lymph node cells are preferable.

ii) Cell Fusion

To obtain hybridomas, cell fusion is performed between the antibody-producing cells thus obtained from the immunized animals and myeloma cells.

Generally obtainable cell lines from animals such as mice can be used as the myeloma cells to be fused with the antibody-producing cells. Preferable cell lines used have drug selectivity and possess the property of being inviable in the unfused state in a HAT selective medium (which contains hypoxanthine, aminopterin, and thymine) but viable only in the state fused with the antibody-producing cells. Moreover, those derived from animals of the same species as the immunized animals are preferable as the cell lines. Concrete examples of the myeloma cells include hypoxanthine-guanine-phosphoribosyl-transferase (HGPRT)-deficient P3X63-Ag.8 (ATCC TIB9), P3X63-Ag.8.U1 (Japanese Collection of Research Bioresources (JCRB) 9085), P3/NSI/1-Ag4-1 (JCRB 0009), P3x63Ag8.653 (JCRB 0028), and Sp2/0-Ag14 (JCRB 0029) cell lines derived from BALB/c mice.

Next, the myeloma cells and the antibody-producing cells are subjected to cell fusion. The cell fusion is carried out by mixing the antibody-producing cells and the myeloma cells at a ratio of approximately 1:1 to 20:1 in a medium for animal cell culture such as serum-free DMEM and RPMI-1640 media and performing fusion reaction in the presence of a cell fusion accelerator. For example, polyethylene glycol with an average molecular weight of 1,500 to 4,000 daltons can be used at a concentration of approximately 10 to 80% as the cell fusion accelerator. To enhance fusion efficiency, an auxiliary substance such as dimethyl sulfoxide may be used together therewith in some cases. Furthermore, a commercially available cell fusion apparatus utilizing electric stimulation (e.g., electroporation) can be used to fuse the antibody-producing cells and the myeloma cells.

iii) Hybridoma Selection and Cloning

Hybridomas of interest are selected from the cells after the cell fusion treatment. A method thereof comprises appropriately diluting a cell suspension with, for example, a fetal bovine serum-containing RPMI-1640 medium, seeding the resulting solution at approximately $2 \times 10^5$ cells/well onto a microtiter plate, adding a selective medium to each well, and performing culture by replacing the selective medium at appropriate time intervals. A culture temperature is 20 to 40° C., preferably approximately 37° C. When the myeloma cells are HGPRT-deficient or thymidine kinase (TK)-deficient cell lines, only hybridomas from the cells having the ability to produce antibodies and the myeloma cells can be cultured and grown selectively by using a selective medium containing hypoxanthine, aminopterin, and thymidine (HAT medium). As a result, cells that start to grow approximately 14 days after the initiation of culture in the selective medium can be obtained as hybridomas.

Next, the presence or absence of antibodies of interest in the culture supernatants of the grown hybridomas is screened. The screening of the hybridomas may be performed according to a usual method and is not particularly limited. For example, a portion of the culture supernatants of the grown hybridomas contained in the wells is collected and screened by Enzyme Immuno Assay (EIA and ELISA), Radio Immuno Assay (RIA), or the like.

The fused cells are cloned by a limiting dilution method or the like to eventually establish hybridomas (monoclonal antibody-producing cells). The hybridoma of the present invention, as described below, is stable in culture in a basal medium such as RPMI1640 and DMEM and produces and secretes the monoclonal antibody specifically reacting with the U7 polypeptide derived form urothelial cancer.

iv) Collection of Monoclonal Antibody

For example, a usual cell culture method or ascites formation method can be adopted as a method for collecting monoclonal antibodies from the established hybridomas.

In the cell culture method, the hybridomas are cultured for 2 to 10 days under typical culture conditions (e.g., 37° C., 5% $CO_2$ concentration) in an animal cell culture medium such as 10% fetal bovine serum-containing RPMI-1640 medium, MEM medium, or serum-free medium, and antibodies are acquired from the resulting culture supernatant.

In the ascites formation method, the hybridomas are intraperitoneally administered at approximately $1 \times 10^7$ cells/animal to animals of the same species as the mammals from which the myeloma cells are derived, to grow the hybridomas in large quantities. After one to two weeks, ascites or serum is collected.

When these methods for collecting antibodies require antibody purification, the purified monoclonal antibody of the present invention can be obtained by appropriately selecting methods known in the art such as ammonium sulfate precipitation, ion-exchange chromatography, affinity chromatography, and gel chromatography or combining these methods.

To prepare the polyclonal antibody, animals are immunized in the same way as above. After 6 to 60 days from the final immunization day, an antibody titer is measured by Enzyme immuno Assay (EIA and ELISA), Radio immuno Assay (RIA), or the like. Anti-serum is obtained by collecting blood on a day when the highest antibody titer is exhibited. Then, the reactivity of polyclonal antibodies in the anti-serum is measured by ELISA or the like.

When the antibody against the U7 polypeptide is used to detect cancer by detecting the expression of the U7 polypeptide in the sample derived from the test subject, a test is conducted on the presence or absence of the antigenic polypeptide in the sample of the test subject, which binds to the antibody against the U7 polypeptide or a labeled antibody thereof. The test subject whose sample contains this antigenic polypeptide is judged as a patient with cancer or an individual at high risk for cancer. Namely, since the antibody or labeled antibody used here is an antibody specifically binding to the U7 polypeptide expressed in cancer cells, the sample containing the antigenic polypeptide that binds to this antibody can be judged as a sample from a patient with solid cancer or a patient at high risk for solid cancer. In this procedure, the binding of, preferably 2 or more kinds, more preferably 5 or more kinds, even more preferably 10 or more kinds, most preferably 15 to 39 kinds of antibodies with the U7 polypeptide in the sample is tested.

In another aspect, a method is used, wherein the binding of the antibody with the U7 polypeptide is performed in a liquid-phase system. For example, the labeled antibody is brought into contact with the sample to bind the labeled antibody to the U7 polypeptide, and this conjugate is separated in the same way as above to detect a label signal in the same way.

In an alternative detection method using the liquid-phase system, the antibody against the U7 polypeptide (primary antibody) is brought into contact with the sample to bind the primary antibody to the antigenic polypeptide, and this conjugate is allowed to bind to the labeled antibody (secondary antibody) to detect a label signal from the conjugate of these three substances. Alternatively, to further increase a signal, an unlabeled secondary antibody may be allowed to bind first to the antibody-antigenic polypeptide conjugate and then to a labeling substance. Such binding of the labeling substance to the secondary antibody can be performed, for example, by biotinylating the secondary antibody and avidinating the labeling substance. Alternatively, an antibody (tertiary antibody) that recognizes a partial region (e.g., Fc domain) of the secondary antibody may be labeled and allowed to bind to the secondary antibody. Monoclonal antibodies can be used as both the primary and secondary antibodies, or otherwise, either of the primary or secondary antibodies can be a polyclonal antibody. The separation of the conjugate from the liquid phase and the detection of a signal can be performed in the same way as above.

In another aspect, a method is used, wherein the binding of the antibody with the U7 polypeptide is tested in a solid-phase system. This method using the solid-phase system is a preferable method by virtue of the detection of trace amounts of the U7 polypeptide and simplified procedures. Namely, this method using the solid-phase system is a method comprising immobilizing the antibody against the U7 polypeptide (primary antibody) onto a solid phase (e.g., resin plates, membranes, or beads), binding the U7 polypeptide to this immobilized antibody, removing unbound peptide by washing, and binding the labeled antibody (secondary antibody) to the antibody-U7 polypeptide conjugate remaining on the plate to detect a signal from this secondary antibody. This method is a so-called "sandwich method", which has been used widely as ELISA when an enzyme is used as a marker. Monoclonal antibodies can be used as both the primary and secondary antibodies, or otherwise, either of the primary or secondary antibodies can be a polyclonal antibody. The detection of a signal can be performed in the same way as above.

The sample is not particularly limited as long as the U7 polypeptide is expressed therein. Urine, serum, cell homogenates, tissue slices, saliva, feces, sputums, pleural effusion, ascites, cerebrospinal fluids, vaginal fluids, or the like can be used as the sample. When cancer such as bladder cancer, ureteral cancer, renal pelvic cancer, and urethral cancer is detected, it is preferred that urine should be used as the sample. When cancer such as lung cancer, gastric cancer, and colon cancer is detected, it is preferred that serum should be used as the sample. When cancer such as gastric cancer and colon cancer is detected, it is preferred that feces and ascites should be used as the sample. When lung cancer is detected, it is preferred that sputums and pleural effusion should be used as the sample.

(2) Detection with U7 Polypeptide

Since the U7 polypeptide is a polypeptide expressed by cancer cells, an antibody against the U7 polypeptide expressed is present in a sample of a test subject with cancer. Thus, the U7 polypeptide can be used to detect the expression of the U7 polypeptide in the test subject by examining its reaction with the antibody in the sample. The U7 polypeptide or the fragment thereof described as an immunogen in the paragraph (1) can be used as the U7 polypeptide used here. A method for producing the U7 polypeptide is as described above.

To detect the expression of the U7 polypeptide in the sample derived from the test subject by use of the U7 polypeptide, a test is conducted on the presence or absence of one or more kinds of antibodies binding to the U7 polypeptide in the sample of the test subject. The test subject whose sample contains the antibody is judged as a patient with cancer or an individual at high risk for cancer. Namely, the U7 polypeptide is a polypeptide that binds to the antibody derived from a patient with cancer. Therefore, as a result of its reaction with the sample of the test subject, the test subject can be judged as a patient with cancer or a patient at high risk for cancer when the sample contains the antibody binding to these antigenic polypeptides. Other cancer markers (e.g., CEA, Cyfra, and SCC-Ag) already known can further be used together therewith. Moreover, the same samples as those described in the paragraph (1) can be used.

A specific method for detecting the U7 polypeptide is performed, for example, by bringing the sample derived from the test subject into contact with the U7 polypeptide and reacting the U7 polypeptide with the antibody in the sample derived from the test subject in a liquid phase. A labeled antibody specifically binding to the antibody in the sample may further be reacted therewith to detect a signal from the labeled antibody. An enzyme, radioactive isotope, or fluorescent dye can be employed as the label used for the labeled antibody. The enzyme is not particularly limited as long as it satisfies conditions such as a high turnover number, stability in binding with the antibody, and specific coloring of its substrate. An enzyme used in usual Enzyme Immuno Assay (EIA), for example, peroxidase, β-galactosidase, alkaline phosphatase, glucose oxidase, acetylcholine esterase, glucose-6-phosphate dehydrogenase, or malate dehydrogenase can be used. Alternatively, an enzyme inhibitor, coenzyme, or the like can also be used. The binding of these enzymes with the antibody can be performed by a method known in the art using a crosslinking agent such as maleimide compounds. A substance known in the art can be used as a substrate according to the types of the enzymes used. For example, 3,3',5,5'- tetramethylbenzidine and para-nitrophenol can be used for peroxidase and alkaline phosphatase, respectively, used as the enzyme.

When the enzyme is used, a substrate that develops color through its degeneration by enzymatic action is added, and enzyme activity is determined by optically measuring the amount of the substrate degenerated, and then converted to the amount of bound antibodies to calculate an antibody level in comparison with a standard value.

Any of those used in usual Radio Immuno Assay (RIA) such as $^{125}$I and $^{3}$H can be used as the radioactive isotope. When the radioactive isotope is used, a radiation dose from the radioactive isotope is measured with a scintillation counter or the like.

Any of those used in usual fluorescent antibody techniques such as fluorescence isothiocyanate (FITC) and tetramethylrhodamine isothiocyanate (TRITC) can be used as the fluorescent dye. When the fluorescent dye is used, the amount of fluorescence may be measured with a measurement apparatus combined with a fluorescence microscope.

The labeled antibody also encompasses those bound with metal such as manganese and iron. The presence of the antibody in serum, that is, the expression of the U7 polypeptide, can be detected by administering such a metal-bound antibody into the body and measuring the metal by MRI or the like.

For example, western blot analysis can be adopted in the detection of a signal. Alternatively, the antigenic polypeptide-serum antibody-labeled antibody conjugate may be separated by a separation means known in the art (e.g., chromatography, salting-out, alcohol precipitation, enzyme, and solid phase methods) to detect a signal from the labeled antibody.

Alternatively, the U7 polypeptide or the fragment thereof can be immobilized on a solid phase (e.g., plates, membranes, and beads) to test its binding with the antibody in the serum of the test subject on this solid phase. Unbound labeled binding molecules can be removed easily by immobilizing the antigenic polypeptide on the solid phase.

(3) Detection with Primer or Probe

The detection method of the present invention can be practiced with a primer or probe comprising the sequence of the whole or a portion of the polynucleotide encoding the U7 polypeptide, or a complementary sequence thereof. The primer or probe can specifically bind to the mRNA of the antigenic polypeptide expressed in a sample derived from a test subject or to cDNA synthesized from the mRNA and thereby detect the expression of the gene encoding the antigenic polypeptide, that is, the expression of the antigenic polypeptide, in the sample.

The primer and probe can be designed according to an approach generally known by those skilled in the art. For example, points to keep in mind for the primer and probe design can be pointed out as follows:

The substantially functional length of the primer is preferably 10 or more bases, more preferably 16 to 50 bases, even more preferably 20 to 30 bases. The substantially functional length of the probe is preferably 10 or more bases, more preferably 16 to 50 bases, even more preferably 20 to 30 bases.

For design, it is preferred that the melting temperature (Tm) of the primer or probe should be confirmed. Tm means a temperature at which 50% of arbitrary polynucleotide chains form hybrids with their complementary strands. The double strand formation and annealing or hybridization between template DNA or RNA and the primer or probe require optimizing an annealing or hybridization temperature. On the other hand, when this temperature is lowered too much, non-specific reaction occurs. Therefore, it is desirable that the temperature should be as high as possible. Thus, the Tm of the primer or probe to be designed is an important factor in performing amplification reaction or hybridization. Software for primer or probe design known in the art can be utilized in the confirmation of Tm. Examples of software available in the present invention include Oligo™ (manufactured by National Biosciences Inc., US) and GENETYX (manufactured by Software Development Co., Ltd, Japan). Alternatively, Tm can also be confirmed by manual calculation without the use of software. In this case, a calculation formula based on a nearest neighbor method, Wallace method, GC % method, or the like can be utilized. In the present invention, average Tm is preferably approximately 45 to 55° C.

Additional conditions that allow for specific annealing or hybridization as the primer or probe include GC contents, and such conditions are well known by those skilled in the art.

The primer and probe thus designed can be prepared according to a method generally known by those skilled in the art. Furthermore, the primer or probe may contain sequences other than the annealing or hybridization region, for example, additional sequences such as tag sequences, as well known by those skilled in the art. The scope of the present invention also encompasses the primer or probe described above, which is supplemented with such additional sequences.

To detect the expression of the U7 polypeptide in the sample derived from the test subject, the primer and/or probe are used in amplification reaction and/or hybridization reaction, respectively. The resulting amplification product or hybridization product is detected.

For example, urine, blood, cell homogenates, tissue slices, saliva, feces, sputums, pleural effusion, ascites, cerebrospinal fluids, and vaginal fluids can be used as the sample. To perform amplification reaction or hybridization reaction, a test nucleic acid is usually prepared from the sample derived from the test subject. The test nucleic acid may be DNA or RNA as long as it is a nucleic acid. The DNA or RNA can be extracted by appropriately using a method well known in the art. For example, a method using phenol extraction and ethanol precipitation or a method using glass beads can be utilized for extracting the DNA, while a guanidine-caesium chloride ultracentrifugation method, hot phenol method, or acid guanidinium thiocyanate-phenol-chloroform (AGPC) method can be utilized for extracting the RNA. The sample or test nucleic acid thus prepared is used to perform amplification reaction and/or hybridization reaction illustrated below.

The primer is used to perform amplification reaction using the test nucleic acid as a template. The expression of the U7 polypeptide in the sample can be detected by detecting the specific amplification reaction.

An amplification means is not particularly limited, and examples thereof can include methods known in the art that utilizes the principles of polymerase chain reaction (PCR), for example, PCR, LAMP (Loop-mediated isothermal Amplification), ICAN (Isothermal and Chimeric primer-initiated Amplification of Nucleic acids), RCA (Rolling Circle Amplification), LCR (Ligase Chain Reaction), and SDA (Strand Displacement Amplification) methods. The amplification is performed until the amplification product reaches a detectable level.

For example, the PCR method uses the test nucleic acid DNA as a template and synthesizes a nucleotide sequence between a pair of primers by DNA polymerase. The PCR method can exponentially amplify amplified fragments by repeating a cycle consisting of denaturation, annealing, and synthesis. The optimum PCR conditions can be determined easily by those skilled in the art.

In RT-PCR, first, RNA serving as the test nucleic acid is used as a template to prepare cDNA by reverse transcriptase reaction. Then, the prepared cDNA is used as a template to perform the PCR method using a pair of primers.

Quantitative detection is made possible by adopting a quantitative PCR method such as competitive PCR and real-time PCR methods as an amplification approach.

To detect the presence or absence of specific amplification reaction after carrying out the amplification reaction, a means known in the art that is capable of specifically recognizing the amplification product obtained by the amplification reaction can be used. The specific amplification reaction can be detected by using, for example, agarose gel electrophoresis to confirm whether or not an amplified fragment of a particular size has been amplified.

Alternatively, a labeling material such as a radioactive isotope, fluorescent substance, and luminescent substance can be allowed to act on dNTP to be incorporated during amplification reaction to detect this labeling material. For example, $^{32}P$, $^{125}I$, or $^{35}S$ can be used as the radioactive isotope. For example, fluorescein (FITC), sulforhodamine (SR), or tetramethylrhodamine (TRITC) can be used as the fluorescent substance. Luciferin or the like can be used as the luminescent substance.

The types, introduction methods, and so on of these labeling materials are not particularly limited, and a variety of means conventionally known in the art can be used. Examples of the introduction methods of the labeling materials include a random prime method using radioactive isotopes.

A method for observing the amplification product that has taken up the labeled dNTP may be any method known in the art for detecting the labeling material. For example, when the radioactive isotope is used as a labeling material, radioactivity can be measured with, for example, a liquid scintillation counter or γ-counter. When fluorescence is used as a labeling material, the fluorescence can be detected with a fluorescence microscope, fluorescence plate reader, or the like.

If the specific amplification reaction is detected in this way, it is determined that the gene encoding the U7 polypeptide has been expressed in the sample. This means that the U7 polypeptide has been expressed. Thus, the test subject whose sample has expressed the U7 polypeptide is judged as a patient with cancer or an individual at high risk for cancer.

Alternatively, the expression of the U7 polypeptide can be detected by performing hybridization reaction with the probe for the sample or test nucleic acid and detecting the specific binding (hybrid) between them.

The hybridization reaction must be performed under conditions that allow the probe to specifically bind to only the polynucleotide derived from the U7 polypeptide, that is, stringent conditions. Such stringent conditions are well known in the art and are not particularly limited. Examples of the stringent conditions include conditions at a sodium concentration of 10 to 300 mM, preferably 20 to 100 mM, and a temperature of 25 to 70° C., preferably 42 to 55° C.

To perform hybridization, an appropriate label such as a fluorescent label (e.g., fluorescein and rhodamine), radioactive label (e.g., $^{32}P$), enzyme label (e.g., alkaline phosphatase and horseradish peroxidase), and biotin label can be added to the probe. Thus, the kit for solid cancer diagnosis of the present invention also comprises the probe supplemented with such a label.

Detection using the labeled probe comprises bringing the sample or test nucleic acid prepared therefrom into contact with the probe so as to cause hybridization between them. The phrase "so as to cause hybridization" means in an environment (temperature, salt concentration) where specific binding occurs under the stringent conditions. Specifically, the sample or test nucleic acid is immobilized on an appropriate solid phase such as a slide glass, membrane, and microtiter plate, to which the label-supplemented probe is then added to perform the hybridization reaction of the probe brought into contact with the sample or test nucleic acid. After the removal of unhybridized probes, the label of the probe hybridized with the sample or test nucleic acid is detected. If the label is detected, the U7 polypeptide has been expressed in the sample. Thus, the test subject whose sample has expressed the U7 polypeptide is judged as a patient with cancer or an individual at high risk for cancer.

Alternatively, quantitative detection is made possible by using the label concentration as an index. Examples of the detection method using the labeled probe can include southern hybridization, northern hybridization, and FISH (fluorescence in situ hybridization) methods.

A specific criterion of judgement in the detection method of the present invention as described in the paragraphs (1) to (3) is the expression level of the U7 polypeptide in the test subject 10% or more, preferably 30% or more, more preferably 70% or more, most preferably 100% or more, higher than that in a normal individual.

The present invention also relates to a diagnostic drug for cancer for use in the detection method. Namely, the diagnostic drug of the present invention comprises a reagent for detecting the expression of a U7 polypeptide selected from, for example, (1) the antibody specifically reacting with the U7 polypeptide or a fragment thereof, (2) the U7 polypeptide, and (3) the polynucleotide encoding the U7 polypeptide, as described above.

The present invention also relates to a kit for cancer diagnosis comprising the diagnostic drug for cancer. A variety of kits according to the types of test components are commercially available as such a kit. The kit for cancer diagnosis of the present invention can also be composed of each element used in the kits known and used in the art, except that the reagent for detecting the expression of a U7 polypeptide (U7 polypeptide, antibody, primer, probe, etc) is used. The kit may contain, for example, a labeled secondary antibody, carrier, washing buffer, sample diluent, enzyme substrate, reaction stop solution, and standard substance, in addition to the reagent for detecting the expression of a U7 polypeptide.

3. Cell Growth Inhibitor and Pharmaceutical Composition for Treating or Preventing Cancer The present inventors have found that the U7 polypeptide is expressed in a manner specific to cancer cells. The present inventors have further found that when the U7 polypeptide-encoding gene is introduced into a variety of cells, difference in cell growth is seen between the positive group transfected with the gene and a control group. It has also been found that cell viability is remarkably decreased by inhibiting the expression of the U7 polypeptide in cancer cells, whereas no significant influence is exerted on the cell viability of normal cells where U7 polypeptide expression has been inhibited in the same way.

Based on these findings, the present inventors have found that cell growth, particularly cancer cell growth, can be suppressed by inhibiting the function or expression of the U7 polypeptide and that the canceration of cells and progression thereof can be treated or prevented by inhibiting the function or expression of the U7 polypeptide.

Namely, the present invention relates to a cell growth inhibitor comprising a reagent inhibiting the function or expression of a U7 polypeptide as an active ingredient and to a pharmaceutical composition for treating or preventing cancer comprising the cell growth inhibitor. Examples of the reagent inhibiting the function or expression of a U7 polypeptide include the followings:

(1) Antibody Specifically Reacting with U7 Polypeptide or Fragment Thereof

The antibody specifically reacting with the U7 polypeptide or a fragment thereof can specifically bind to the U7 polypeptide in a test subject and thereby inhibit its activity. Thus, a pharmaceutical composition comprising an antibody against the U7 polypeptide is effective for the treatment or prevention of cancer. The antibody specifically reacting with the U7 polypeptide or a fragment thereof is as described above.

(2) Reagent Capable of Inhibiting Expression of Gene Encoding U7 Polypeptide

Examples of the reagent capable of inhibiting the expression of a gene encoding the U7 polypeptide include an expression vector available for substituting the transcriptional promoter region of the gene in a targeted test subject with a promoter that inhibits the transcription. Alternatively, an expression vector for inserting a nucleotide sequence with transcription-inhibitory activity to a region involved in the transcription of the gene encoding the U7 polypeptide may be used as the reagent capable of inhibiting the transcription of the gene encoding the U7 polypeptide. The design and preparation of these expression vectors are well known by those skilled in the art.

Alternative examples of the reagent capable of inhibiting the expression of a gene encoding the U7 polypeptide include so-called antisense RNA, a gene encoding (i.e., transcribing) the RNA, and a vector comprising the gene. For example, a gene transcribing antisense RNA against the mRNA of the gene is introduced in the form of a plasmid or incorporated into the genome of the test subject, and translation of the mRNA of the gene encoding the U7 polypeptide is inhibited by overexpression of the antisense RNA.

The action of the antisense RNA to inhibit target gene expression includes several factors as follows: the inhibition of transcription initiation by triplex formation; transcription inhibition by hybrid formation with a site where an open loop structure is locally formed by RNA polymerase; transcription inhibition by hybrid formation with RNA during its synthesis; splicing inhibition by hybrid formation at intron-exon boundaries; splicing inhibition by hybrid formation with a spliceosome formation site; the inhibition of nuclear-cytoplasmic transport by hybrid formation with mRNA; splicing inhibition by hybrid formation with a capping or polyA-addition site; the inhibition of translation inhibition by hybrid formation with a translation initiation factor-binding site; translation inhibition by hybrid formation with a ribosome-binding site in proximity to the initiation codon; the inhibition of peptide chain elongation by hybrid formation with a mRNA coding region or polysome-binding site; and the inhibition of gene expression by hybrid formation with a nucleic acid-protein interaction site. As described above, the antisense nucleic acid inhibits various processes such as transcription, splicing, or translation and thereby suppresses target gene expression (Hirashima and Inoue, "New Biochemistry Experimentation Lectures 2, Nucleic Acids IV, Replication and Expression of Genes", ed. The Japanese Biochemical Society, Tokyo Kagaku Dozin, pp. 319-347, 1993).

The antisense sequence used in the present invention may inhibit the target gene expression by any of the actions described above. In one aspect, an antisense sequence designed to be complementary to non-coding region in proximity to the 5' end of the mRNA of the gene is considered to be effective for the inhibition of gene translation. Moreover, a sequence complementary to the coding region or 3'-non-coding region can also be employed. As described above, the antisense DNA utilized in the present invention also encompasses DNAs comprising antisense sequences against not only the translated region of the gene but also the untranslated region thereof. The antisense DNA used is ligated downstream of an appropriate promoter. Preferably, a sequence containing a transcription termination signal is ligated on its 3' side. The antisense DNA sequence is preferably a sequence complementary to an endogenous gene carried by a transformant or to a portion thereof but does not have to be completely complementary thereto as long as it can effectively inhibit gene expression. The transcribed RNA has preferably 90% or higher complementarity, most preferably 95% or higher complementarity, to the transcript of the target gene. To effectively inhibit target gene expression by use of the antisense sequence, the antisense DNA is at least 15 or more bases, preferably 100 or more bases, even more preferably 500 or more bases, in length. The length of antisense DNA usually used is shorter than 5 kb, preferably shorter than 2.5 kb.

Techniques as to antisense RNA for, for example, mammals used as hosts are also known (Han et al. (1991) Proc. Natl. Acad. Sci. USA, 88, 4313-4317; and Hackett et al. (2000) Plant Physiol., 124, 1079-86).

DNA encoding a ribozyme is also available for inhibiting the expression of the gene encoding the U7 polypeptide. Thus, in one aspect of the present invention, the cell growth inhibitor comprises a ribozyme against the gene encoding the U7 polypeptide as an active ingredient. The ribozyme refers to an RNA molecule having catalytic activity. The ribozyme includes those having a variety of activities. Among others, research focusing on a ribozyme acting as an enzyme that cleaves RNA has allowed for the design of a ribozyme site-specifically cleaving RNA. Some ribozymes such as group I intron ribozymes and M1 RNA contained in RNase P are 400 or more nucleotides in size, and others are called hammerhead or hairpin ribozymes, which have active domains on the order of 40 nucleotides (Koizumi M and Otsuka E, "Protein, Nucleic acid and Enzyme", 35: 2191, 1990).

For example, the self-cleaving domain of the hammerhead ribozyme cleaves the 3' side of C15 in a G13U14C15 sequence, and the base pairing of U14 and A9 has been said to be important for its activity. It has been shown that A15 or U15 instead of C15 is cleavable (Koizumi M, et al., FEBS Lett 228: 228, 1988). If a ribozyme is designed to have a substrate-binding site complementary to the RNA sequence adjacent to the target site, a restriction enzyme-like RNA-cleaving ribozyme that recognizes a UC, UU, or UA sequence in the target RNA can be constructed (Koizumi M, et al., FEBS Lett 239: 285, 1988; Koizumi M and Otsuka E., "Protein, Nucleic acid and Enzyme", 35: 2191, 1990; and Koizumi M, et al., Nucl. Acids Res 17: 7059, 1989).

The hairpin ribozyme is also useful for the object of the present invention. This ribozyme is found in, for example, the minus strand of tobacco ringspot virus satellite RNA (Buzayan, J M., Nature 323: 349, 1986). It has also been shown that a target-specific RNA-cleaving ribozyme can be constructed from the hairpin ribozyme (Kikuchi Y, Sasaki N, Nucl. Acids Res 19: 6751, 1991; and Kikuchi Y, "Chemistry and Biology" 30: 112, 1992).

The ribozyme designed to be capable of cleaving the target is ligated to a promoter (e.g., cauliflower mosaic virus 35S promoter) and transcription termination sequence so that it is transcribed in a cell. The ribozyme activity is sometimes lost if a redundant sequence is added to the 5' end or 3' end of the transcribed RNA. In such a case, to accurately cleave only the ribozyme portion from the transcribed RNA containing the ribozyme, another cis-acting trimming ribozyme may be located on the 5' side or 3' side of the ribozyme portion (Taira K, et al., Protein Eng 3: 733, 1990; Dzianott A M, Bujarski J J, Proc Natl Acad Sci USA 86: 4823, 1989; Grosshans C A, Cech T R, Nucl Acids Res 19: 3875, 1991; and Taira K, et al., Nucl Acids Res 19: 5125, 1991). Moreover, the effect can be increased more by arraying such constitutional units in tandem to be capable of cleaving several sites within the target gene (Yuyama N, et al., Biochem Biophys Res Commun 186: 1271, 1992). As described above, the expression of the U7 polypeptide-encoding gene in the present invention can be inhibited by specifically cleaving the transcript of the gene with the ribozyme.

RNA interference (RNAi) is also available for inhibiting the expression of the gene encoding the U7 polypeptide. Specifically, when double-stranded RNA complementary to the targeted nucleotide sequence of the gene encoding the U7 polypeptide is introduced into a cell, the mRNA of an endogenous gene encoding the U7 polypeptide is degraded, with the result that the gene expression is specifically inhibited in the cell. This approach has also been demonstrated in mammal cells (Hannon, G J., Nature (2002) 418, 244-251 (review); JP Patent Publication (Kohyo) No. 2002-516062A (2002); and JP Patent Publication (Kohyo) No. 8-506734A (1996)). The gene used in RNAi does not have to be completely identical to the target gene and has at least 70% or higher, preferably 80% or higher, more preferably 90% or higher, most preferably 95% or higher sequence identity. The sequence identity can be determined by the approach described above.

Thus, in one aspect, the cell growth inhibitor of the present invention comprises, as an active ingredient, a reagent selected from double-stranded RNA decreasing a U7 polypeptide-encoding mRNA level, DNA encoding the double-stranded RNA, and a vector comprising the DNA. The double-stranded RNA is preferably siRNA, and specific examples thereof include double-stranded RNA consisting of RNA (sense strand) comprising the nucleotide sequence represented by SEQ ID NO: 1 and RNA (antisense strand) comprising the nucleotide sequence represented by SEQ ID NO: 2, double-stranded RNA consisting of RNA (sense strand) comprising the nucleotide sequence represented by SEQ ID NO: 3 and RNA (antisense strand) comprising the nucleotide sequence represented by SEQ ID NO: 4, double-stranded RNA consisting of RNA (sense strand) comprising the nucleotide sequence represented by SEQ ID NO: 5 and RNA (antisense strand) comprising the nucleotide sequence represented by SEQ ID NO: 6, double-stranded RNA consisting of RNA (sense strand) comprising the nucleotide sequence represented by SEQ ID NO: 7 and RNA (antisense strand) comprising the nucleotide sequence represented by SEQ ID NO: 8, double-stranded RNA consisting of RNA (sense strand) comprising the nucleotide sequence represented by SEQ ID NO: 9 and RNA (antisense strand) comprising the nucleotide sequence represented by SEQ ID NO: 10, and double-stranded RNA consisting of RNA (sense strand) comprising the nucleotide sequence represented by SEQ ID NO: 11 and RNA (antisense strand) comprising the nucleotide sequence represented by SEQ ID NO: 12. The double-stranded RNA consisting of RNA (sense strand) comprising the nucleotide sequence represented by SEQ ID NO: 1 and RNA (antisense strand) comprising the nucleotide sequence represented by SEQ ID NO: 2 is preferable.

The double-stranded RNA of the present invention also encompasses RNA comprising a nucleotide sequence having at least 80%, preferably at least 90%, more preferably at least 95% homology to the nucleotide sequence represented by each SEQ ID NO described above. Each of the RNAs is usually composed of 16 to 26 bases, preferably 19 to 23 bases, more preferably 21 bases.

The double-stranded RNA decreasing a U7 polypeptide-encoding mRNA level, the DNA encoding the double-stranded RNA, and the vector comprising the DNA are well known by those skilled in the art and described in, for example, Experimental Medicine Suppl., Notable Bio Experiment Series "RNAi Experimental Protocol", ed. Taira K, et al, Yodosha Co., Ltd, issued by Apr. 1, 2003.

The present inventors have found that cell growth suppression specific to cancer cells and the inhibition of cancer cell survival can be achieved by inhibiting the function or expression of the U7 polypeptide. Thus, the cell growth inhibitor of the present invention can be used as a pharmaceutical composition for preventing or treating cancer.

The cancer to which the pharmaceutical composition of the present invention is applied is preferably solid cancer including, but not limited to, lung cancer, colon cancer, gastric cancer, breast cancer, prostatic cancer, uterine cancer, choriocarcinoma, kidney cancer, thyroid cancer, parotid gland cancer, head and neck cancer, brain tumor, bone and soft tissue sarcomas, liver cancer, ovarian cancer, fallopian tube cancer, esophagus cancer, gastric cancer, and urothelial cancer (renal pelvic cancer, ureteral cancer, bladder cancer, and urethral cancer). Preferably, the cancer is lung cancer, colon cancer, breast cancer, prostatic cancer, uterine cancer, choriocarcinoma, urothelial cancer, more preferably urothelial cancer, particularly preferably bladder cancer.

The pharmaceutical composition of the present invention can be administered for the purpose of preventing the onset of these cancers or for the purpose of preventing the aggravation of symptoms or alleviating symptoms for patients with these cancers or patients diagnosed as being at high risk for the cancers.

The administration modes of the cell growth inhibitor and the pharmaceutical composition of the present invention are, preferably, usual systemic administration such as intravenous and intraarterial administration as well as local administration such as local injection.

The cell growth inhibitor and the pharmaceutical composition of the present invention can be used, for example, in the form of a sterile solution with water or a pharmaceutically acceptable liquid or of an injection of a suspension. Moreover, they can be made into a preparation in appropriate combination with, for example, a pharmaceutically acceptable carrier or medium, specifically, sterilized water or a saline, emulsifier, suspending agent, surfactant, stabilizer, vehicle, and antiseptic.

A sterile composition for injection can be formulated according to a usual method for producing a preparation by using a vehicle such as distilled water for injection. Examples of an aqueous solution for injection include salines and isotonic solutions containing glucose or other adjuvants, for example, D-sorbitol, D-mannose, D-mannitol, and sodium chloride, which may be used together with an appropriate solubilizing agent, for example, alcohol, specifically ethanol or polyalcohol (e.g., propylene glycol or polyethylene glycol), and a non-ionic surfactant, for example, Polysorbate 80™ or HCO-50. Examples of an oil solution include sesame oil and soybean oil, which may be used together with benzyl benzoate or benzyl alcohol as a solubilizing agent. Moreover, a buffer (e.g., phosphate buffer solution or sodium acetate buffer solution), soothing agent (e.g., procaine hydrochloride), stabilizer (e.g., benzyl alcohol or phenol), and antioxidant may be mixed therewith. The prepared solution for injection is usually filled into an appropriate ampule.

The dose thereof can be selected appropriately depending on the age and conditions of a patient. For example, one dose may be selected within the range of 0.0001 mg to 1000 mg/kg of body weight. Alternatively, for example, the dose can be selected within the range of 0.001 to 100000 mg/patient. However, the therapeutic drug of the present invention is not limited to these dose ranges.

The dose differs depending on the age, sex, and conditions of a patient, an administration route, the number of doses, and a dosage form and can be adjusted appropriately by those skilled in the art or physicians.

The present specification encompasses contents described in the specification and/or drawings of Japanese Patent Application No. 2004-164844 that serves as a basis for the priority of the present application.

BRIEF DESCRIPTION OF THE DRAWINGS

FIG. 1A shows a result for bladder cancer tissue used (pH 4.5 to 5.5, 12.5% gel). FIG. 1B shows a magnified view of the box shown in FIG. 1A (the arrow shows a U7 spot). FIG. 1C shows a result for normal urothelial tissue used, which corresponds to FIG. 1B. The spot U7 indicated by the arrow appears for the urothelial cancer tissue used as a sample (FIG. 1A), whereas this spot is not seen for the normal urothelial tissue (FIG. 1C);

FIG. 2A (top column) is a result of examining U7 polypeptide expression in human urinary tract tissue obtained by surgery, wherein T and N are results for bladder cancer tissue and normal urothelial tissue, respectively. A band corresponding to U7 can be observed in the cancer tissue but not in the normal tissue. FIGS. 2B (middle column) and 2C (lower column) are, respectively, a result of U7 expression in a variety of cancer cell lines. 5637, HT1197, J82, RT112, SBT31A, SCaBER, DSH-1, T24, TCCSUP, and UM-UC-3: bladder cancer, WI38: normal fibroblast, BeWo: choriocarcinoma, AZ521: gastric cancer, Caski: uterine cancer, RERF-LC-MS: lung cancer, LoVo: colon cancer, AGS: gastric cancer, DLD-1: colon cancer, A549: lung cancer, PC3: prostatic cancer, LNCaP: prostatic cancer, HeLa: uterine cancer;

FIG. 4A is a result of confirming the inhibition of expression through RNA interference by western blot. FIG. 4B is a result of a test of cell growth inhibition through RNA interference.

BEST MODE FOR CARRYING OUT THE INVENTION

Hereinafter, the present invention will be described more fully with reference to Examples. However, the scope of the present invention is not intended to be limited to them.
Procedures
1. Sample Bladder cancer tissue and normal urothelial tissue excised by surgery were used in proteome analysis or western blot. Moreover, 10 kinds of bladder cancer cell lines, 11 kinds of cancer cell lines other than bladder cancer, and normal fibroblast WI38 cells were separately cultured, and their respective lysates were used in western blot. Rat fibroblast Rat1 cells, mouse fibroblast NIH3T3 cells, and rat embryonic fibroblast REF cells were used in a gene transfer experiment. Uterine cancer cell line HeLa cells and normal human dermal fibroblast (NHDF) cells were used in an experiment of gene function inhibition using siRNA (short interfering RNA).

2. Proteome Analysis

Tissue proteins were separated by narrow pH range two-dimensional electrophoresis, followed by the visualization of protein spots by silver staining. Cancer-specific spots were detected with two-dimensional electrophoresis gel analysis software, and the proteins forming the spots were identified by a peptide mass fingerprinting method (Yoshiki, et al. Application of Proteomics Techniques in Urological Field, Advanced Medicine Series 24/Urology, Latest Medical Care for Urologic Diseases, Advanced Medical Technology Research Center, pp. 47-54, 2003; and Kageyama, et al. Clinical Chemistry, 50: 857-866, 2004).

3. Preparation of Anti-U7 Monoclonal Antibody

BALB/c mice were immunized with GST-fused U7 polypeptides expressed in *Escherichia coli* as immunogens to prepare anti-U7 monoclonal antibodies (Yoshiki, et al. Acta Urologica Japonica 39: 213-9, 1993).

4. Western Blot

Western blot was performed with the anti-U7 monoclonal antibodies to confirm the presence or absence of the expression of U7 polypeptides derived from each tissue or cell. To confirm the amount of the antigen added, anti-β-actin antibodies were used.

5. Gene Transfer by Lipofection Method

Canceration ability was investigated by gene-transferring a pCR3.1-FLAG-U7 vector to the Rat1 cells by use of Lipofectamine Plus Reagent (Invitrogen) and overexpressing U7.

6. Gene Transfer with Retrovirus

A pCX4-FLAG-U7 vector was constructed and transfected into Bosc23 packaging cells by use of Lipofectamine Plus Reagent A culture supernatant containing retrovirus produced was collected. The Rat1, NIH3T3, and REF cells were infected with the virus by adding this culture supernatant thereto. Only gene-transferred cells were selected in a medium supplemented with blastcidin.

Figure 1:
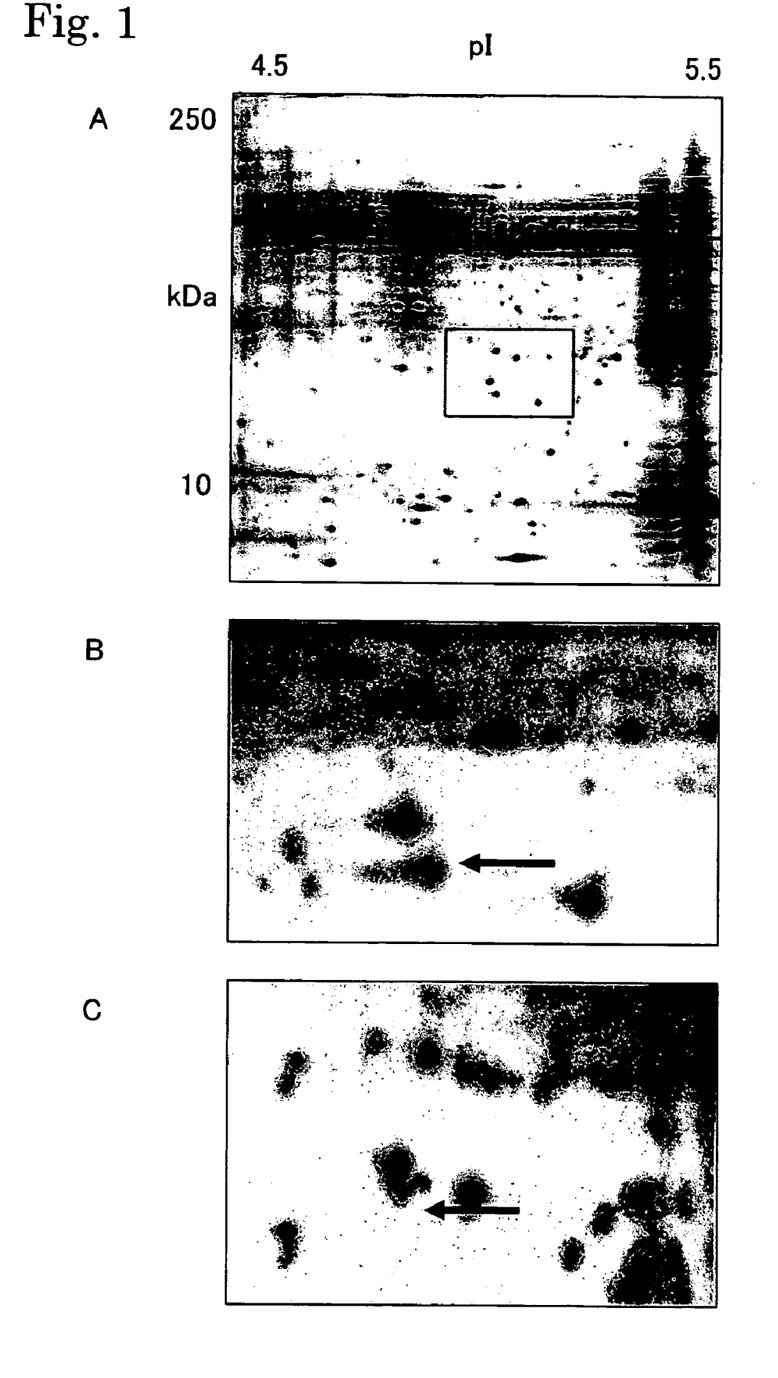
FIG. 1 shows a result of two-dimensional electrophoresis using urothelial tissue.

7. Experiment of U7 Function Inhibition Through RNA Interference siRNAs (short interfering RNAs: custom-designed and synthesized by Qiagen) were prepared and introduced into the HeLa cells by use of Lipofectamine 2000 to confirm the inhibition of U7 polypeptide expression by western blot. The siRNA that had the best inhibition efficiency was used and introduced into the HeLa and NHDF cells to compare the degrees of cell growth inhibition by modified MTT assay using siRNA against luciferase GL-3 as a negative control.
Results
1. Identification of U7 Polypeptide Fifteen spots were detected as those having expression enhanced by cancer by way of the comparison of the silver-stained two-dimensional gel electrophoretograms between the bladder cancer and normal urothelial tissues. Of them, the spot with a molecular weight of approximately 22 kDa and an isoelectric point of approximately 5.1 was designated as U7 (FIG. 1). This spot was cleaved out, then enzymatically treated, and subjected to a peptide mass fingerprinting method, thereby showing that it was a hypothetical polypeptide C7orf24 (chromosome 7 open reading frame 24) on the protein database (Accession number: NP076956).

2. U7 Polypeptide Expression in a Variety of Cells

Figure 2:
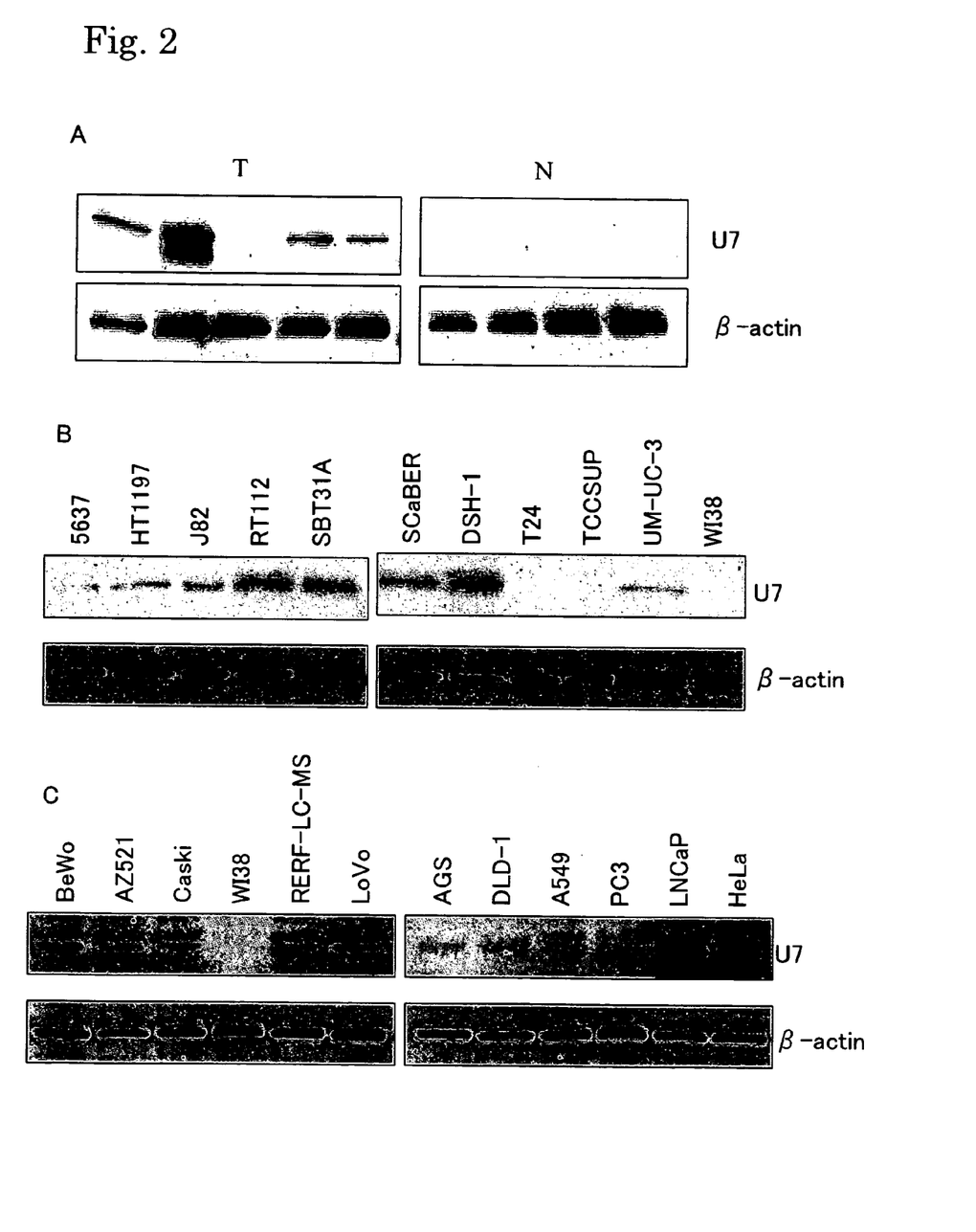
FIG. 2 shows a result of western blot with anti-U7 antibodies.

The recombinant U7 polypeptides were used as immunogens to establish anti-U7 monoclonal antibodies (clone 6.1E). In the western blot of the bladder cancer (T) and normal bladder (N) tissues, the enhanced expression was observed in the cancer tissue as compared with the normal tissue (FIG. 2A). In the investigation using the normal urothelial tissues, polypeptide bands corresponding to U7 were positive in 3 out of 10 cases but very slightly reactive. By contrast, for the tissues of cancer portions, the obvious appearance of bands was observed in 16 out of 22 cases. The U7 polypeptide was also confirmed in 3 out of 8 cases of urine from patients with bladder cancer. U7 polypeptide expression was observed in 8 out of 10 kinds of bladder cancer cell lines. This expression was also observed in all of 11 kinds of cell lines (lung cancer, gastric cancer, colon cancer, breast cancer, prostatic cancer, uterine cancer, and choriocarcinoma) in addition to bladder cancer. However, no U7 band was observed in the normal fibroblast WI38 (FIG. 2B). Immunostaining demonstrated that the normal cells were stained very slightly, whereas the cancer cells had strong positive reaction in their cytoplasms and nuclei.

3. Canceration Ability Analysis in Transient Overexpression System

Canceration ability analysis was conducted by allowing the rat normal fibroblast Rat1 cells to express U7 polypeptides. A result pointing to canceration ability was not obtained in focus assay and soft agar assay.

4. Investigation in Stable Expression System

Figure 3:
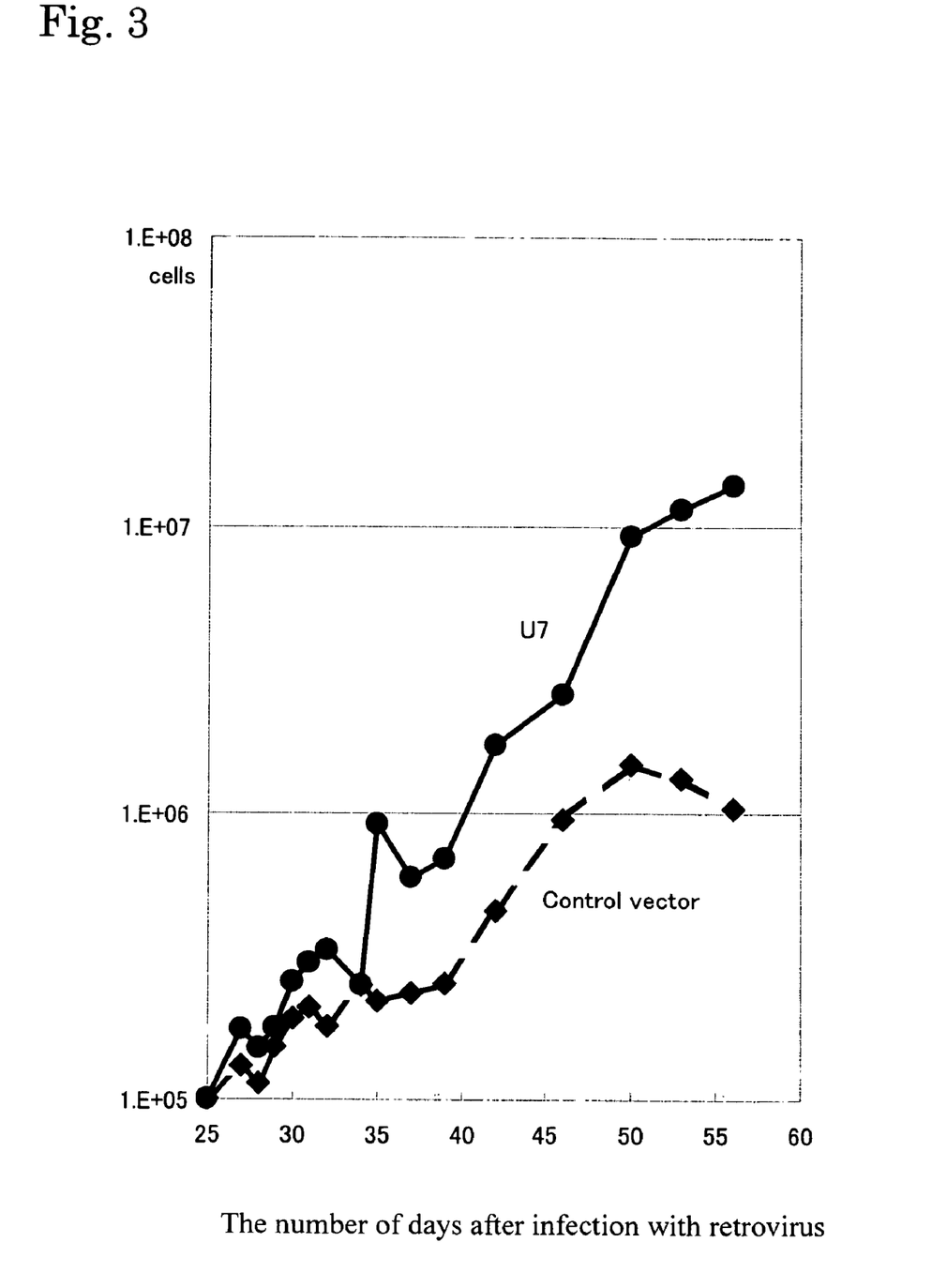
FIG. 3 shows a result of U7 gene transfer to rat embryonic fibroblast (REF) cells.

The stable expression system of U7 polypeptides was established with retrovirus in the REF cells that have been observed to stop proliferating during long-term culture. Then, long-term subculture was carried out. A growth curve dating from the 25th day is shown in FIG. 3 with the day of viral infection defined as the 1st day. The U7-expressing REF cells transfected with the U7 genes exhibited more upward trend in growth ability than the REF cells infected with control vectors. Furthermore, the REF cells infected with control vectors stopped proliferating around day 50 (50th day), whereas the U7-expressing REF cells transfected with the U7 genes still continued to proliferate and exhibited the trend toward immortalization.

5. Experiment of U7 Function Inhibition Through RNA Interference (RNAi)

Figure 4:
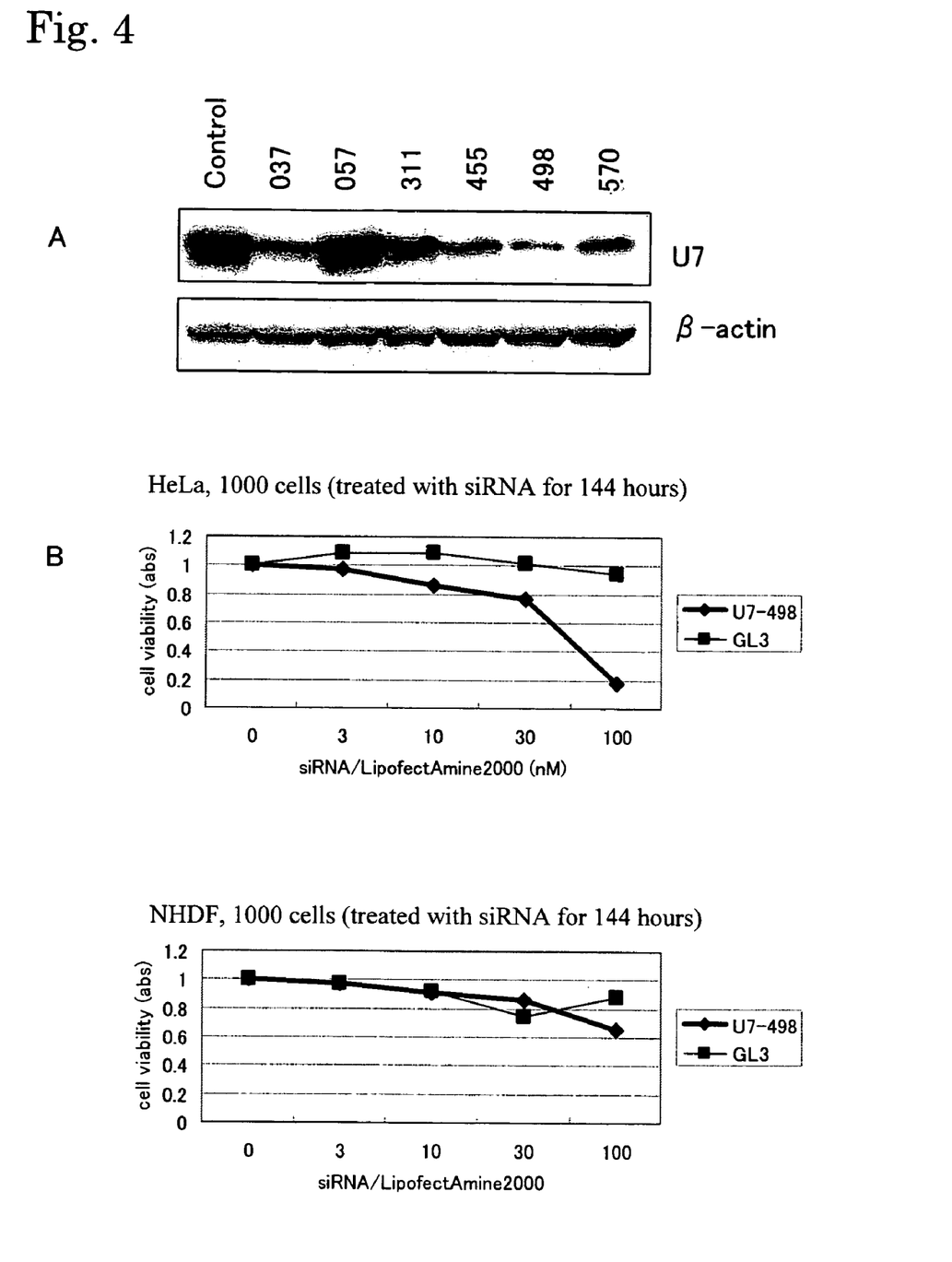
FIG. 4 shows a result of an experiment of U7 function inhibition through RNA interference.

Six kinds of siRNAs were prepared to perform western blot. The results are shown in FIG. 4A. The results of inhibition of U7 polypeptide expression by each sequence were 39% by 037 (SEQ ID NOS: 3 and 4), 102% by 057 (SEQ ID NOS: 5 and 6), 25% by 570 (SEQ ID NOS: 7 and 8), 62% by 311 (SEQ ID NOS: 9 and 10), 30% by 455 (SEQ ID NOS: 11 and 12), and 9% by 498 (SEQ ID NOS: 1 and 2), with that by a control defined as 100.

Each siRNA sequence is shown in Table 1 below. The sequences shown below correspond to SEQ ID NOS: 3 through 12, 1 and 2, respectively.

TABLE 1

| | |
|---|---|
| 37-sense | 5'-GAUGAGGAGAGUUUUCUGUdTdT-3' |
| 37-antisense | 5'-ACAGAAAACUCUCCUCAUCdTdT-3' |
| 57-sense | 5'-CUUUGCCUACGGCAGCAACdTdT-3' |
| 57-antisense | 5'-GUUGCUGCCGUAGGCAAAGdTdT-3' |
| 570-sense | 5'-CAUAACAGAAUAUAUCUAAdTdT-3' |
| 570-antisense | 5'-UUAGAUAUAUUCUGUUAUGdTdT-3' |
| 311-sense | 5'-UGUAUGUUGUAAUAGAAGUdTdT-3' |
| 311-antisense | 5'-ACUUCUAUUACAACAUACAdTdT-3' |
| 455-sense | 5'-UGCCGCUGGAGUAUCAAGAdTdT-3' |
| 455-antisense | 5'-UCUUGAUACUCCAGCGGCAdTdT-3' |
| 498-sense | 5'-UGACUAUACAGGAAAGGUCdTdT-3' |
| 498-antisense | 5'-GACCUUUCCUGUAUAGUCAdTdT-3' |

Based on this result, the siRNA with the highest inhibitory effect on U7 expression was selected (U7-498: sense strand 5'-UGACUAUACAGGAAAGGUCdTdT-3' (SEQ ID NO: 1); and antisense strand 5'-GACCUUUCCU-GUAUAGUCAdTdT-3') (SEQ ID NO: 2). This U7-498 was used to perform a test of U7 function inhibition. The viability of the uterine cancer cell line HeLa cells where U7 function was inhibited by the siRNA (U7-498) was decreased to approximately ⅕ that of the cells where U7 function was not inhibited (upper diagram of FIG. 4B). By contrast, no significant difference was observed in the viability of the normal human dermal fibroblast NHDF even when its U7 function was inhibited or not inhibited (lower diagram of FIG. 4B).

All publications, patents, and patent applications cited herein are incorporated herein by reference in their entirety.

INDUSTRIAL APPLICABILITY

According to the present invention, means effective for the effective detection of cancer, the inhibition of cancer cell growth, and the prevention or treatment of cancer are provided.

The invention claimed is:

1. A cell growth inhibitor comprising as an active ingredient a polynucleotide reagent that inhibits expression of SEQ ID NO:13, wherein the reagent inhibiting the expression is:
   (1) a double-stranded RNA that decreases the SEQ ID NO:13 mRNA level through RNA interference, and the double-stranded RNA consists of RNA that is 19 to 23 nucleotides in length having at least 90% homology to SEQ ID NO: 1 and RNA that is 19 to 23 nucleotides in length having at least 90% homology to SEQ ID NO: 2; or
   (2) a DNA encoding a double-stranded RNA that decreases the SEQ ID NO:13 mRNA level through RNA interference, and the double-stranded RNA consists of RNA that is 19 to 23 nucleotides in length having at least 90% homology to SEQ ID NO:1 and RNA that is 19 to 23 nucleotides in length having at least 90% homology to SEQ ID NO:2.

2. A composition comprising a cell growth inhibitor according to claim 1.

3. Double-stranded RNA consisting of RNA that is 19 to 23 nucleotides in length having at least 90% homology to SEQ ID NO: 1 and RNA that is 19 to 23 nucleotides in length having at least 90% homology to SEQ ID NO: 2.

4. DNA encoding double-stranded RNA according to claim 3.

5. A vector comprising DNA according to claim 4.

6. The cell growth inhibitor according to claim 1, wherein the double-stranded RNA consists of RNA consisting of SEQ ID NO: 1 and RNA consisting of SEQ ID NO: 2.

7. Double-stranded RNA according to claim 3, which consists of RNA consisting of SEQ ID NO: 1 and RNA consisting of SEQ ID NO: 2.

* * * * *

SEQUENCE LISTING

<160> NUMBER OF SEQ ID NOS: 14

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 1
ugacuauaca ggaaaggucn n                                              21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 2
gaccuuuccu guauagucan n                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 3
gaugaggaga guuuucugun n                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 4
acagaaaacu cuccucaucn n                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 5
cuuugccuac ggcagcaacn n                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature

```
<222> LOCATION: (20)..(21)
<223> OTHER INFORMATION: n = deoxythymidine

<400> SEQUENCE: 6
guugcugccg uaggcaaagn n                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine e

<400> SEQUENCE: 7
cauaacagaa uauaucuaan n                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 8
uuagauauau ucuguuaugn n                                              21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 9
uguauguugu aauagaagun n                                              21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 10
acuucuauua caacauacan n                                              21

<210> SEQ ID NO 11
<211> LENGTH: 21
<212> TYPE: RNA
<213> ORGANISM: Artificial Sequence
```

```
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 11
ugccgcugga guaucaagan n                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: synthetic
      RNA
<220> FEATURE:
<221> NAME/KEY: misc_feature
<222> LOCATION: (20)..(21)
<223> OTHER INFORMATION: n = deoxythymidine

<400> SEQUENCE: 12
ucuugauacu ccagcggcan n                                              21

<210> SEQ ID NO 13
<211> LENGTH: 188
<212> TYPE: PRT
<213> ORGANISM: Homo sapiens

<400> SEQUENCE: 13

Met Ala Asn Ser Gly Cys Lys Asp Val Thr Gly Pro Asp Glu Glu Ser
 1               5                  10                  15

Phe Leu Tyr Phe Ala Tyr Gly Ser Asn Leu Leu Thr Glu Arg Ile His
             20                  25                  30

Leu Arg Asn Pro Ser Ala Ala Phe Phe Cys Val Ala Arg Leu Gln Asp
         35                  40                  45

Phe Lys Leu Asp Phe Gly Asn Ser Gln Gly Lys Thr Ser Gln Thr Trp
     50                  55                  60

His Gly Gly Ile Ala Thr Ile Phe Gln Ser Pro Gly Asp Glu Val Trp
 65                  70                  75                  80

Gly Val Val Trp Lys Met Asn Lys Ser Asn Leu Asn Ser Leu Asp Glu
                 85                  90                  95

Gln Glu Gly Val Lys Ser Gly Met Tyr Val Val Ile Glu Val Lys Val
            100                 105                 110

Ala Thr Gln Glu Gly Lys Glu Ile Thr Cys Arg Ser Tyr Leu Met Thr
        115                 120                 125

Asn Tyr Glu Ser Ala Pro Pro Ser Pro Gln Tyr Lys Lys Ile Ile Cys
    130                 135                 140

Met Gly Ala Lys Glu Asn Gly Leu Pro Leu Glu Tyr Gln Glu Lys Leu
145                 150                 155                 160

Lys Ala Ile Glu Pro Asn Asp Tyr Thr Gly Lys Val Ser Glu Glu Ile
                165                 170                 175

Glu Asp Ile Ile Lys Lys Gly Glu Thr Gln Thr Leu
            180                 185

<210> SEQ ID NO 14
<211> LENGTH: 1186
<212> TYPE: DNA
<213> ORGANISM: Homo sapiens

<400> SEQUENCE: 14
```

-continued

```
cgccagtccc ctaaccctga ggctgccgcg cggcggtcac tgcgccgggg tagtgggccc    60
cagtgttgcg ctctctggcc gttccttaca ctttgcttca ggctccagtg cagggcgta    120 gtgggatatg gccaactcgg gctgcaagga cgtcacgggt ccagatgagg agagttttct   180
gtactttgcc tacggcagca acctgctgac agagaggatc cacctccgaa acccctcggc   240
ggcgttcttc tgtgtggccc gcctgcagga ttttaagctt gactttggca attcccaagg   300
caaaacaagt caaacttggc atggagggat agccaccatt tttcagagtc ctggcgatga   360
agtgtgggga gtagtatgga aaatgaacaa aagcaattta aattctctgg atgagcaaga   420
aggggttaaa agtggaatgt atgttgtaat agaagttaaa gttgcaactc aagaaggaaa   480
agaaataacc tgtcgaagtt atctgatgac aaattacgaa agtgctcccc catccccaca   540
gtataaaaag attatttgca tgggtgcaaa agaaaatggt ttgccgctgg agtatcaaga   600
gaagttaaaa gcaatagaac caaatgacta tacaggaaag gtctcagaag aaattgaaga   660
catcatcaaa aaggggggaaa cacaaactct ttagaacata acagaatata tctaagggta   720
ttctatgtgc taatataaaa tatttttaac acttgagaac agggatctgg gggatctcca   780
cgtttgatcc gttttcagca gtgctctgaa ggagtatctt acttgggtga ttccttgttt   840
ttagactata aaaagaaact gggataggag ttagacaatt taaaaggggt gtatgagggc   900
ctgaaatatg tgacaaatga atgtgagtac cccttctgtg aacactgaaa gctattctct   960
tgaattgatc ttaagtgtct ccttgctctg gtaaaagata gatttgtagc tcacttgatg  1020
atggtgctgg tgaattgctc tgctctgtct gagattttta aaaatcagct taatgagagt  1080
aatctgcaga caattgataa taacattttg aaaattggaa agatggtata ctgttttag   1140 aggaataaac gtatttgtgg tttaaaaaaa aaaaaaaaa aaaaaa                   1186
```